United States Patent [10] Patent No.: US 10,144,696 B2
Joshi et al. (45) Date of Patent: Dec. 4, 2018

(54) HETEROGENEOUS CATALYST FOR TRANSESTERIFICATION AND METHOD OF PREPARING SAME

(71) Applicant: Crystaphase Products, Inc., Houston, TX (US)

(72) Inventors: Umakant Pravinchandra Joshi, Houston, TX (US); Peter Gregory Ham, Houston, TX (US)

(73) Assignee: CRYSTAPHASE PRODUCTS, INC., Houston, TX (US)

( * ) Notice: Subject to any disclaimer, the term of this patent is extended or adjusted under 35 U.S.C. 154(b) by 0 days.

(21) Appl. No.: 15/130,525

(22) Filed: Apr. 15, 2016

(65) Prior Publication Data

US 2016/0303545 A1 Oct. 20, 2016

Related U.S. Application Data

(60) Provisional application No. 62/149,138, filed on Apr. 17, 2015, provisional application No. 62/155,970, (Continued)

(51) Int. Cl.
*C07C 67/02* (2006.01)
*B01J 27/18* (2006.01)
(Continued)

(52) U.S. Cl.
CPC ............. *C07C 67/02* (2013.01); *B01J 21/066* (2013.01); *B01J 23/04* (2013.01); *B01J 27/1806* (2013.01);
(Continued)

(58) Field of Classification Search
CPC ........... C07C 67/02; C07C 67/04; C11C 3/02; C11C 3/04; B01J 17/1806; B01J 23/04;
(Continued)

(56) References Cited

U.S. PATENT DOCUMENTS 2,084,511 A 6/1937 Small
5,162,589 A 11/1992 Wijngaarden et al.
(Continued)

FOREIGN PATENT DOCUMENTS

EP 3204158 8/2017
WO 2010113011 A2 10/2010
(Continued)

OTHER PUBLICATIONS

European Patent Office; PCT International Search Report, Issued in connection to PCT/US2016/027892; dated Jul. 15, 2015; 4 pages; Europe.
(Continued)

*Primary Examiner* — Yate' K Cutliff
(74) *Attorney, Agent, or Firm* — Greenberg Traurig LLP

(57) ABSTRACT

A transesterification catalyst that is heterogeneous and a method for preparing said transesterification catalyst are provided. The catalyst can be used in a variety of transesterification reactor configurations including CSTR (continuous stirred tank reactors), ebullated (or ebullating) beds or any other fluidized bed reactors, and PFR (plug flow, fixed bed reactors). The catalyst can be used for manufacturing commercial grade biodiesel, biolubricants and glycerin.

11 Claims, 6 Drawing Sheets

Overall Transesterification chemical reaction

Related U.S. Application Data filed on May 1, 2015, provisional application No. 62/320,104, filed on Apr. 8, 2016.

(51) Int. Cl.

| | | |
|---|---|---|
| *B01J 21/06* | (2006.01) | |
| *B01J 23/04* | (2006.01) | |
| *B01J 35/10* | (2006.01) | |
| *C07C 67/03* | (2006.01) | |
| *C10L 1/02* | (2006.01) | |
| *C10M 105/34* | (2006.01) | |
| *C11C 3/00* | (2006.01) | |
| *B01J 37/03* | (2006.01) | |
| *B01J 37/04* | (2006.01) | |
| *B01J 37/08* | (2006.01) | |

(52) U.S. Cl.
CPC ....... *B01J 35/1014* (2013.01); *B01J 35/1057* (2013.01); *B01J 35/1061* (2013.01); *C07C 67/03* (2013.01); *C10L 1/026* (2013.01); *C10M 105/34* (2013.01); *C11C 3/003* (2013.01); *B01J 37/031* (2013.01); *B01J 37/036* (2013.01); *B01J 37/04* (2013.01); *B01J 37/08* (2013.01); *C10L 2200/0476* (2013.01); *C10L 2270/026* (2013.01); *C10L 2290/543* (2013.01); *C10L 2290/547* (2013.01); *Y02E 50/13* (2013.01); *Y02P 20/582* (2015.11)

(58) Field of Classification Search
CPC .............. B01J 27/1806; B01J 35/1014; B01J 35/1057; B01J 35/1061

See application file for complete search history.

(56) References Cited

U.S. PATENT DOCUMENTS

| | | | | |
|---|---|---|---|---|
| 7,528,278 | B2* | 5/2009 | Benderly | B01J 27/10 560/217 |
| 7,741,502 | B2 | 6/2010 | Lecocq et al. | |
| 7,754,643 | B2 | 7/2010 | Srinivas et al. | |
| 7,795,460 | B2 | 9/2010 | Elliott | |
| 7,834,203 | B2* | 11/2010 | Lee | C07C 67/03 44/308 |
| 7,842,653 | B2 | 11/2010 | Darbha et al. | |
| 7,863,494 | B2* | 1/2011 | Kang | B01J 27/1806 208/114 |
| 8,124,801 | B2 | 2/2012 | Srinivas et al. | |
| 8,193,383 | B2* | 6/2012 | Saft | C07C 67/03 554/167 |
| 8,962,873 | B2 | 2/2015 | Summers et al. | |
| 9,085,547 | B2 | 7/2015 | Jonsson et al. | |
| 9,643,163 | B2 | 5/2017 | Joshi et al. | |
| 9,770,707 | B2 | 9/2017 | Glover | |
| 2002/0010359 | A1 | 1/2002 | Kaita et al. | |
| 2008/0257781 | A1* | 10/2008 | Lecocq | B01J 27/16 208/46 |
| 2009/0145022 | A1 | 6/2009 | Ng et al. | |
| 2010/0170143 | A1 | 7/2010 | McNeff et al. | |
| 2011/0185625 | A1* | 8/2011 | Singh | B01J 23/002 44/307 |
| 2011/0245527 | A1 | 10/2011 | Ooms et al. | |
| 2012/0029218 | A1 | 2/2012 | Kim et al. | |
| 2012/0130101 | A1 | 5/2012 | Yoo et al. | |
| 2012/0240452 | A1 | 9/2012 | Erdoes, Jr. et al. | |
| 2013/0164798 | A1 | 6/2013 | Vanhercke et al. | |
| 2014/0046104 | A1 | 2/2014 | McNeff et al. | |
| 2014/0109466 | A1 | 4/2014 | Schmidt et al. | |
| 2014/0206833 | A1 | 7/2014 | Fernandez et al. | |
| 2014/0296583 | A1 | 10/2014 | Frey et al. | |
| 2016/0102041 | A1 | 4/2016 | Joshi et al. | |
| 2017/0043326 | A1 | 2/2017 | Joshi et al. | |
| 2017/0065964 | A1 | 3/2017 | Joshi et al. | |
| 2018/0178202 | A1 | 6/2018 | Joshi et al. | |

FOREIGN PATENT DOCUMENTS

| | | | | |
|---|---|---|---|---|
| WO | WO 2014/190436 | * | 12/2014 | ............ C07C 67/02 |
| WO | 2016057913 | | 4/2016 | |
| WO | 2016168697 | | 10/2016 | |
| WO | 20170177220 | | 10/2017 | |

OTHER PUBLICATIONS

European Patent Office; PCT Written Opinion of the International Searching Authority, Issued in connection to PCT/US2016/027892; dated Jul. 15, 2015; 8 pages; Europe.

Kumar et al.; Phase Assemblage Stucy and Cytocompatibility Property of Heat Treated Potassium Magnesium Phosphate-Silicate Ceramics; 2009; Journal of Mater Sci.; Mater Med. 20; pp. 1689-1695.

Skogareva et al.; Nanostructured Sodium Calcium Tripolyphosphate and its Peroxo Derivatives are a New Generation of Bioceramic Materials; 2011; Russian Journal of Inorganic Chemistry, vol. 56, No. 7; pp. 1004-1011.

Kouzu et al.; Calcium Oxide as a Solid Base Catalyst for Transesterification of Soybean Oil and its Application to Biodiesel Production; Mar. 6, 2007; 9 pages; Elsevier.

Patent Cooperation Treaty; PCT International Search Report, Issued in Connection with PCT/US2015/054930; dated Feb. 2, 2016; 4 pages; European Patent Office; Europe.

Patent Cooperation Treaty; PCT Written Opinion of the International Searching Authority, Issued in Connection with PCT/US2015/054930; dated Feb. 2, 2016; 7 pages; European Patent Office; Europe.

Wen Cheng Chen et al.; "Green Synthesis of Calcium and Phosphate Compounds by Varying pH Value and Ca/P Atomic Ratio Using Aqueous Precipitations," Ceramics-Silikaty; Mar. 1, 2013; pp. 14-21; http://www.ceramics-silikaty.cz/2013/pdf/2013_01_014.pdf.

Yue Y et al.; "Hydrothermal Crystallization and Structural Investigation of Na1+2xZr2—xMgx(P04)3 Systems;" Materials Chemistry and Physics; vol. 35, No. 1; Aug. 1, 1993.

I.K. Lloyd et al.; "Sintering and Characterization of Alkaline-Earth-Doped and Zirconium-Dificient Na3Zr2Si2P012;" Solid State Ionics; vol. 11, No. 1; Sep. 1, 1993; 6 pages; North Holland Publishing Company; Amsterdam, NL.

European Patent Office; PCT International Search Report, Issued in connection to PCT/US2017/026772; dated Jul. 28, 2017; 5 pages; Europe.

European Patent Office; PCT Written Opinion of the International Searching Authority, Issued in connection to PCT/US2017/026772; dated Jul. 28, 2017; 10 pages; Europe.

"Heterogeneous Catalysis"; downloaded from http://www.benefuel.net/technology.php; obtained Nov. 17, 2017 ; 1 page.

Bloch, Michel; Improved Glycerin Quality via Solid Catalyst Transesterification Technology: The Estertip-H Process; Bio-Oil International Conference; Axens IFP Group Technologies; Feb. 2006; 23 pages; http://www.biodieselspain.com/articulos/axens.pdf.

Flint Hills Resources; Duonix Beatrice Begins Commercial-Scale Biodiesel Production Using Innovative Ensel Technology; downloaded from https://www.fhr.com/newsroom/2016/Duonix-Beatrice-Begins-Commercial-Scale-Biodiesel; obtained Nov. 17, 2017; 4 pages.

* cited by examiner

Overall Transesterification chemical reaction

HETEROGENEOUS CATALYST FOR TRANSESTERIFICATION AND METHOD OF PREPARING SAME

RELATED APPLICATIONS

This application claims the benefit, and priority benefit, of U.S. Provisional Patent Application Ser. No. 62/149,138, filed Apr. 17, 2015; U.S. Provisional Patent Application Ser. No. 62/155,970, filed May 1, 2015 and U.S. Provisional Patent Application Ser. No. 62/320,104, filed Apr. 8, 2016 the contents of each of which are incorporated by reference herein in their entirety.

BACKGROUND

1. Field of the Invention

The presently disclosed subject matter relates to a heterogeneous catalyst and use of the heterogeneous catalyst for transesterification.

2. Description of the Related Art

Transesterification is the reversible chemical reaction process of exchanging the organic group of an ester with the organic group of an alcohol. Transesterification processes became commercially popular in the 1940s as researchers explored ways to more readily produce glycerol (also called glycerin, glycerine and propanetriol) used in explosives manufacture during World War II. Currently, transesterification is an important step in industrial processes such as production of: acrylates from methymethacrylate, polyethylene terephthalate (PET) polymer manufacturing from ethylene glycol and either dimethyl terephthalate or terephthalic acid, and alkyl esters. Of particular current commercial interest is the transesterification of alcohol with triglyceride esters contained in oils and fats (primarily vegetable oils and animal fats) to form fatty acid alkyl esters and glycerin. These esters find commercial use as biodiesel fuel and biolubricants.

Catalysts known to facilitate the transesterification reaction include mineral acids and bases, metal alkoxides, non-ionic bases and lipase enzymes. These catalysts include homogeneous species which are soluble in reactants and/or products and heterogeneous species which are solids and insoluble in reactants or products.

Alkaline metal alkoxides (e.g., $CH_3ONa$ for methanolysis) and alkaline metal hydroxides (NaOH and KOH) are catalysts for the homogeneous transesterification reaction. These catalysts are soluble in reactants and products and thus require extensive post-reaction treatment including product neutralization, salt removal and water wash to produce commercially acceptable products. These are non-trivial processes and costly to install, maintain and operate. Homogeneous enzymatic transesterification using lipase has been utilized for conversion of triglycerides to biodiesel, since the byproduct glycerin can be purified by flashing off the excess alcohol from the products. However, processing time can be lengthy for acceptable conversion of triglycerides and product clean-up costs are high to make commercial grade products.

Replacement of the homogeneous catalyst with heterogeneous catalyst has been commercialized notably with the Esterfip-H® process licensed by Axens and the ENSEL® process licensed by Benefuel. These heterogeneous catalyst processes can reduce post-reaction processing, but require reaction operating temperatures of 150 degrees C. to 250 degrees C. and alcohol partial pressure as high as 300 to 400 psi for the manufacture of biodiesel alkyl esters. These heterogeneous catalyst reactions must be carried out in fixed bed reactors due to the severity of the process conditions.

Improvements in this field of technology are desired to reduce the operating severity and costs of the transesterification reaction regime as well as the subsequent process clean-up and product purification steps. Improvements are also desired which allow use of new technology in existing or readily modified commercial facilities.

SUMMARY

According to the various illustrative embodiments provided herein, the presently disclosed transesterification catalyst is a solid, heterogeneous compound having the general formula $ZxQy(PO_4)nH_2O$, where Z is selected from Group 1 metals including potassium, sodium and lithium, Q is selected from Group 2 metals including calcium, magnesium and barium, x is a rational number in the range from 0.5 to 4, y is a rational integer in the range from 2 to 8, and n is a rational integer in the range from 4 to 8, M can be any ceramic substrate such as, for example, zirconia, alumina, or combinations thereof on which the catalyst is supported. The Group 1 and Group 2 alkali metals form a double metal salt catalyst, the phosphate $(PO_4)_n$, makes it insoluble and the ceramic provides the solid support, in certain illustrative embodiments.

In certain illustrative embodiments, the presently disclosed transesterification catalysts can be used in a variety of transesterification reactor configurations including CSTR (continuous stirred tank reactors), ebullated (or ebullating) beds or any other fluidized bed reactors, and PFR (plug flow, fixed bed reactors). The presently disclosed transesterification catalysts can be used for manufacturing commercial grade biodiesel, biolubricants and glycerin.

In certain illustrative embodiments, a compound is provided. The compound can have the formula $ZxQy(PO_4)nH_2O$, wherein Z is selected from the group consisting of potassium, sodium and lithium, Q is selected from the group consisting of calcium, magnesium and barium, x is a rational number in the range from 0.5 to 4, y is a rational integer in the range from 2 to 8, n is a rational integer in the range from 4 to 8, and M is a ceramic substrate on which the catalyst is supported, and wherein the compound is a transesterification catalyst. The total surface area of the compound can be greater than 20 square meters per gram. The active surface area of the compound can be greater than 20 square meters per gram. The average diameter of the pores in the compound can be in the range from 1-10 nanometers, The compound can be active at a temperature in the range from 40 to 70 degrees C. The compound can also be active at a temperature in the range from 40 to 130 degrees C.

In certain illustrative embodiments, a method of preparing a transesterification catalyst is provided. A metal hydro xide with the metal selected from the group consisting of potassium, sodium and lithium can be mixed with a metal hydroxide with the metal selected from the group consisting of calcium, magnesium and barium. The components can be mixed in a ratio of approximately 1:10 by weight to form a component mixture, in certain illustrative embodiments. The component mixture can be dissolved in phosphoric acid and heated to a temperature in the range from 60-90 degrees C. A solid compound can be precipitated and washed. The precipitate can be mixed with ceramic substrate powder in a ratio of approximately 2:10 by weight and washed with water. The precipitate/ceramic substrate mixture can be calcined. Calcination can occur at a temperature in the range from 400-500 degrees C. for 4 hours or greater.

In certain illustrative embodiments, a method of preparing an alkyl ester using a transesterification catalyst is provided. The alkyl ester can be suitable for use as biodiesel fuel, as a biodiesel additive to conventional diesel fuel, or as a biolubricant additive to conventional lubricants. The alkyl ester can also be suitable for use as a biolubricant. A transesterification catalyst can be provided. The catalyst can have the formula $ZxQy(PO_4)nH_2O$, wherein Z is selected from the group consisting of potassium, sodium and lithium, Q is selected from the group consisting of calcium, magnesium and barium, x is a rational number in the range from 0.5 to 4, y is a rational integer in the range from 2 to 8, n is a rational integer in the range from 4 to 8, and M is a ceramic substrate on which the catalyst is supported. Triglycerides and alcohol can be reacted in the presence of said catalyst to convert the triglycerides and alcohol to alkyl ester and glycerin. The triglycerides can be triglyceride-containing fats and/or oils. The conversion can be essentially complete conversion of triglycerides. The glycerin can be separated from the reaction mixture. The reaction mixture can be filtered to recover the catalyst. The unreacted alcohol can be distilled from the alkyl ester and the glycerin. The method can be at least partially performed in a continuous stirred tank reactor. The method can also be at least partially performed in a fixed bed reactor. The method can also be at least partially performed in a fluidized bed reactor. The alkyl ester is capable of being used as biodiesel fuel, a biodiesel additive to conventional diesel fuel, a biolubricant additive to other lubricants or as a biolubricant.

While certain preferred illustrative embodiments will be described herein, it will be understood that this description is not intended to limit the subject matter to those embodiments. On the contrary, it is intended to cover all alternatives, modifications, and equivalents, as may be included within the spirit and scope of the subject matter as defined by the appended claims.

DETAILED DESCRIPTION

For the purposes of this disclosure, the transesterification catalysts of the various illustrative embodiments will hereinafter be referred to as UMAKAT. Various means for transesterification using UMAKAT are also provided. According to the various illustrative embodiments provided herein, UMAKAT is a porous, solid, heterogeneous compound having the general formula $Z_xQ_yPO_nMH_2O$, where Z is selected from Group 1 metals including potassium, sodium and lithium, Q is selected from Group 2 metals including calcium, magnesium and barium, x is a rational number in the range from 0.5 to 4, y is a rational integer in the range from 2 to 8, and n is a rational integer in the range from 4 to 8. M can be any ceramic substrate such as, for example, zirconia, silica, alumina, or combinations thereof. The Group 1 and Group 2 alkali metals form a double metal salt catalyst, the phosphate ($PO_n$) makes it insoluble and the ceramic provides the solid support, in certain illustrative embodiments. UMAKAT's porous structure includes nanometer-sized pores which result in the material having substantial surface area.

Figure 1A:
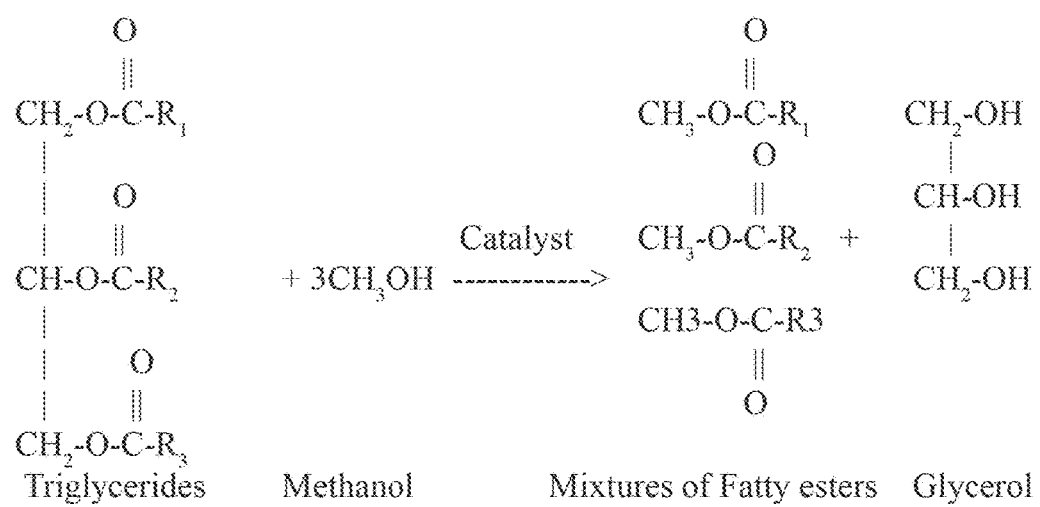
FIGS. 1A and 1B show an illustrative embodiment of a transesterification reaction.
Figure 1B:
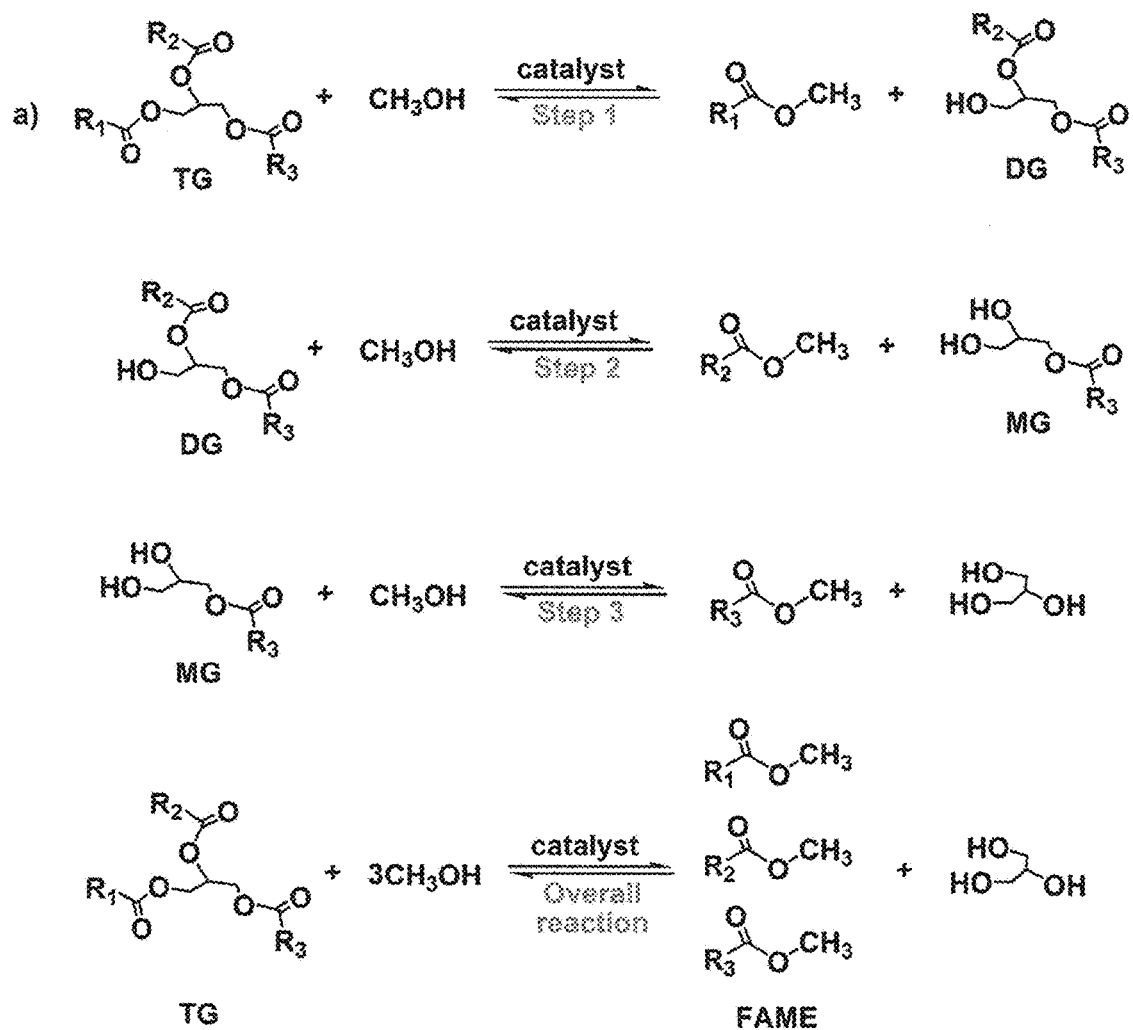
Figure 2:
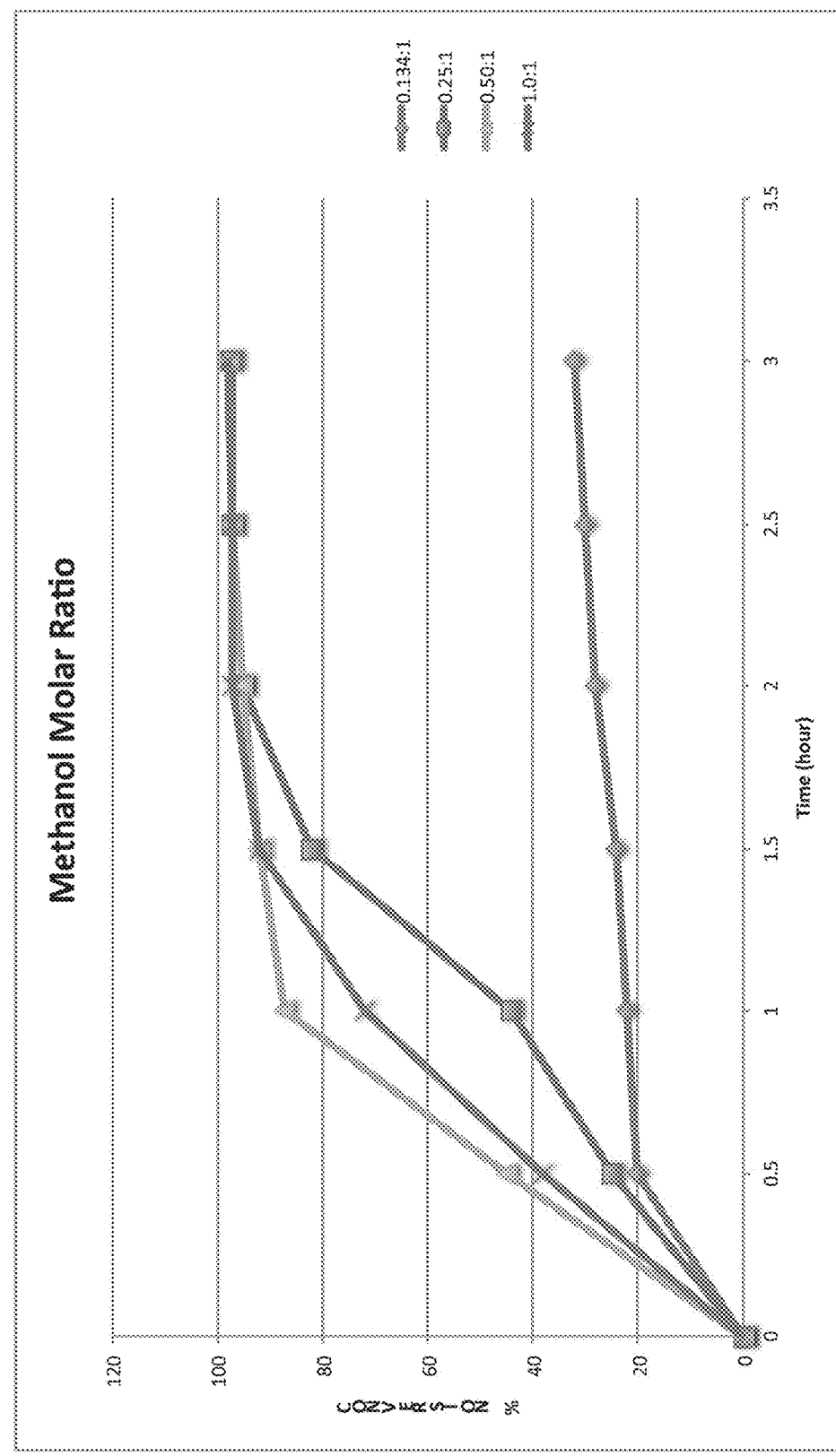
FIG. 2 is a line graph comparing reaction conversion at different methanol molar ratios at 1 weight % of the presently disclosed transesterification catalysts in an illustrative embodiment.
Figure 3:
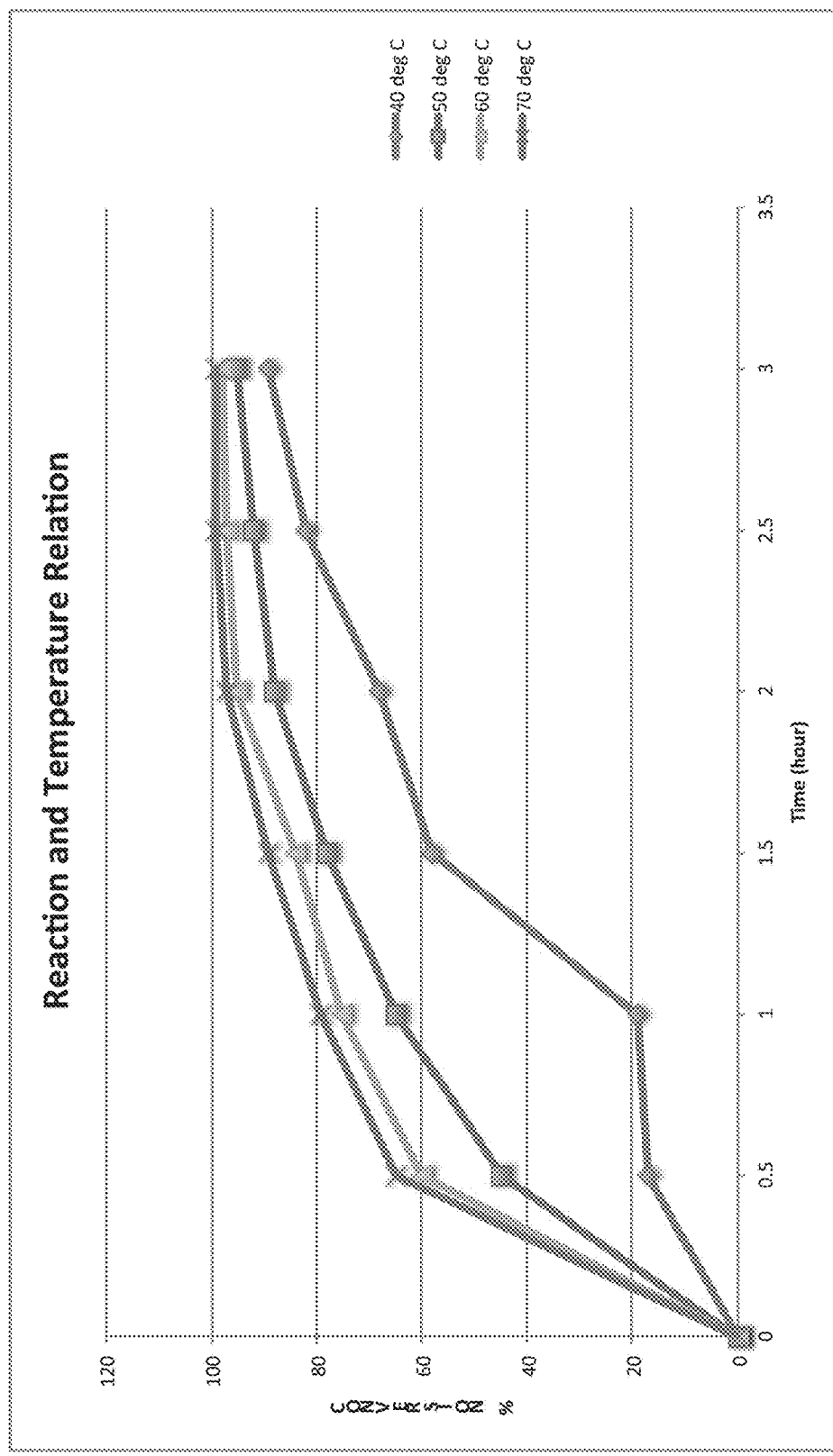
FIG. 3 is a line graph comparing reaction conversion at different temperatures at 1 weight % of the presently disclosed transesterification catalysts in an illustrative embodiment.
Figure 4:
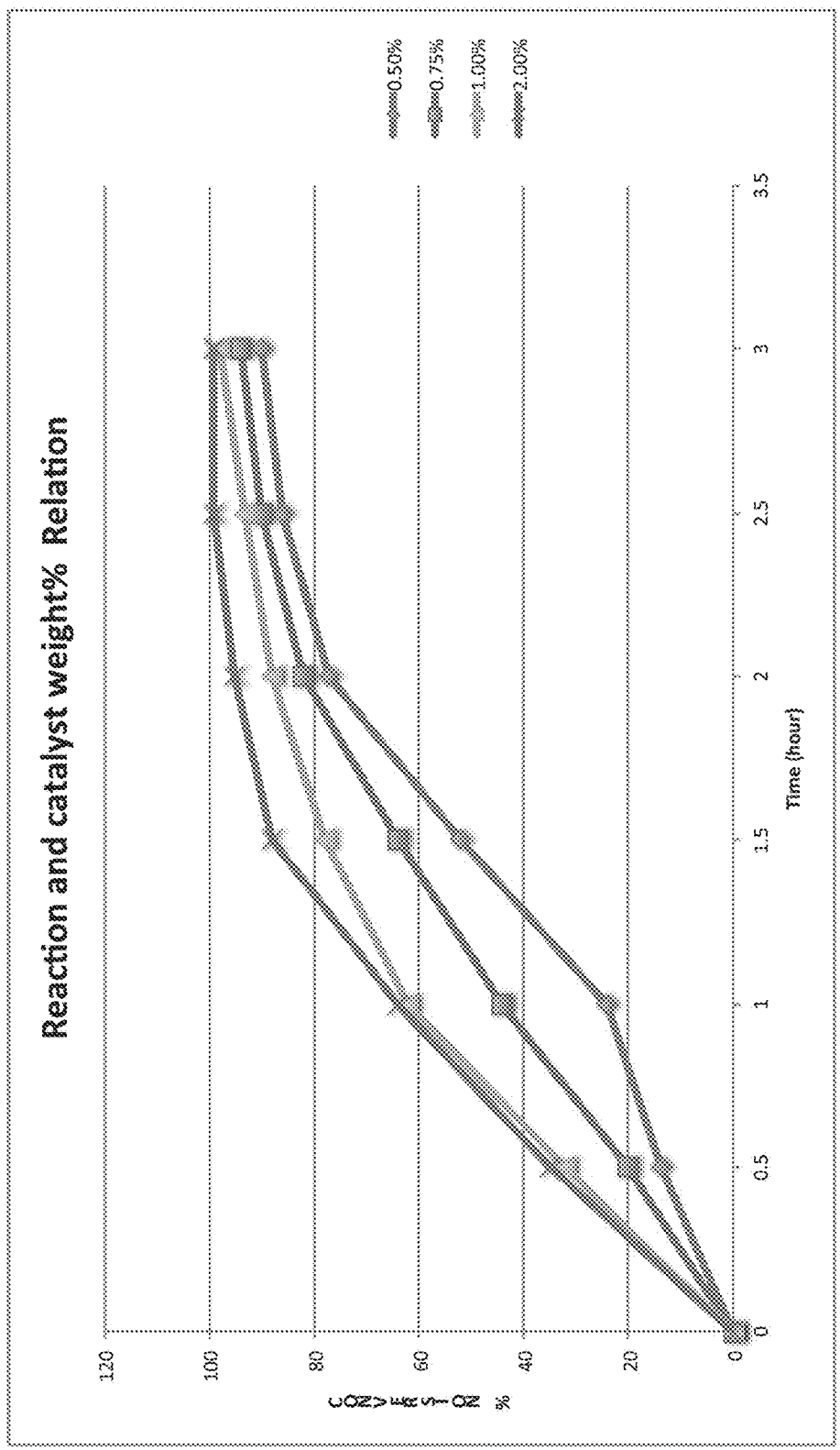
FIG. 4 is a line graph comparing reaction conversion at different weights of the presently disclosed transesterification catalysts at a fixed temperature of 60 degrees C. in an illustrative embodiment.
Figure 5:
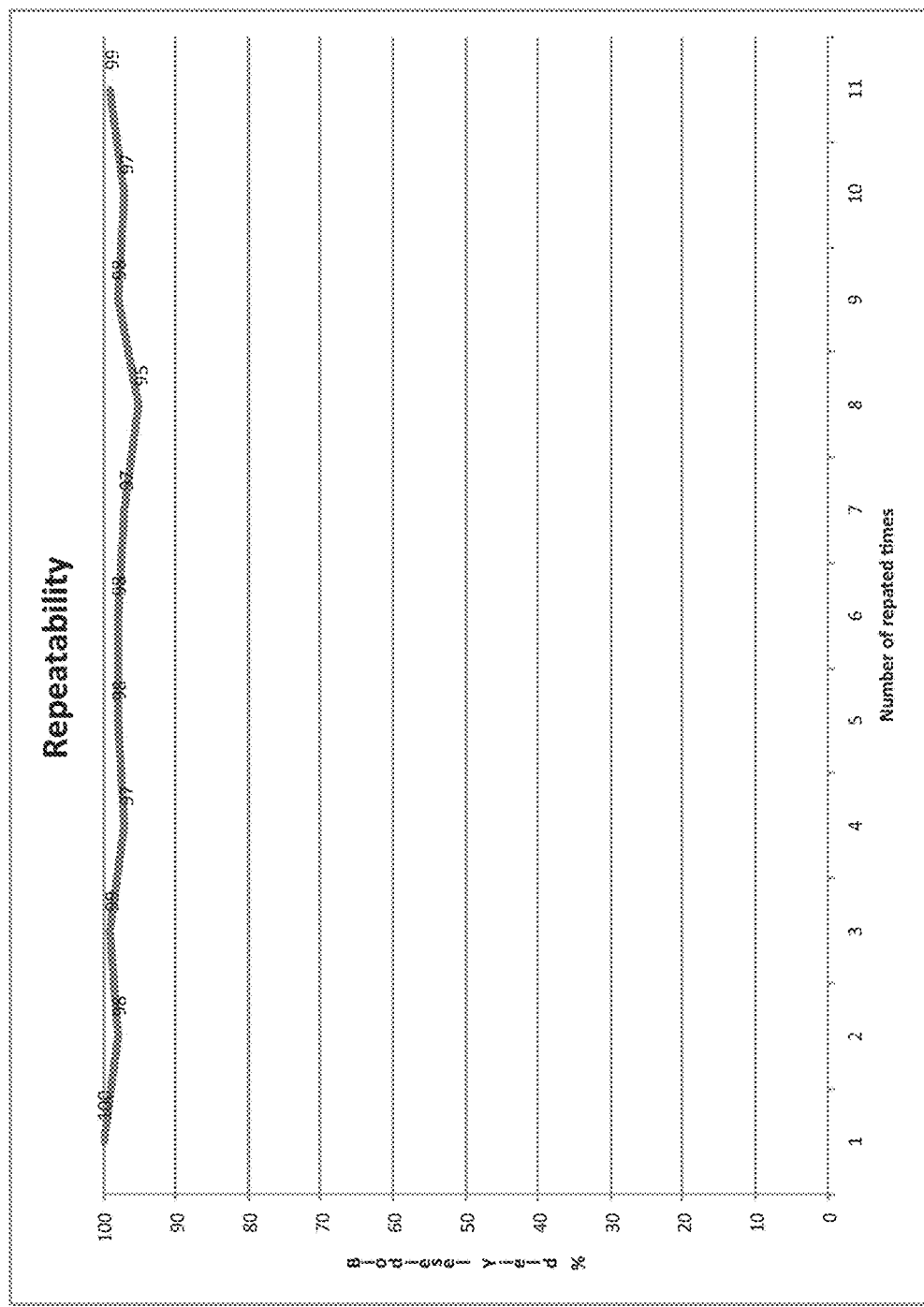
FIG. 5 is a line graph comparing biodiesel (i.e., alkyl ester) yield using the same presently disclosed transesterification catalysts for repeat trials in an illustrative embodiment.

The generic process for the transesterification reaction is shown in FIGS. 1A and 1B. FIG. 1A represents the overall transesterification reaction, while FIG. 1B represents not only the overall reaction but also the stepwise chemical reactions where the triglyceride (TG) ester is first converted to alkyl ester and diglyceride (DG) ester, then the DG ester is converted to alkyl ester and monoglyceride (MG) ester, and then the MG ester is converted to alkyl ester and glycerin.

In certain illustrative embodiments, the presently disclosed transesterification catalysts can have a total surface area greater than 20 m2/gm and an active surface area greater than 20 m2/gm. As used herein, the term "total surface area" means surface area totally available, and the term "active surface area" means surface area available for reaction. The active surface area of the presently disclosed transesterification catalysts is significant because the higher the active surface area, the greater the availability of active catalyst sites.

In certain illustrative embodiments, the heterogeneous compound can be porous. For example, the presently disclosed transesterification catalysts can have an average pore diameter in the range from 1-10 nanometers (Nm). Pore diameter is measured by nitrogen adsorption. The pore diameter of the presently disclosed transesterification catalysts is sufficient to allow migration or diffusion of reactant molecules into and out of the pores of the presently disclosed transesterification catalysts, in certain illustrative embodiments. This will determine the rate and extent of absorption of reactant molecules at the catalyst surfaces.

Other homogeneous transesterification processes call for the catalyst being dissolved in an alcohol, for example, methanol or ethanol, which needs to be removed post reaction. Further, the homogeneous catalyst is soluble in reactants and products, which requires steps to cleanse the alkyl ester and glycerin products. In contrast, in certain illustrative embodiments the presently disclosed transesterification catalysts can form a slurry with triglyceride-containing oils and/or fats rather than alcohol for a better reaction conversion and easier separation of reactants and catalyst at the end of the reaction. In general, a catalyst slurry can be made with any oil/fat rather than methanol/ethanol solution (or any other alcohol) for CSTR type reactions. Further, in certain illustrative embodiments the presently disclosed transesterification catalyst provides a uniform suspension throughout the reaction media. By comparison, a heterogeneous catalyst suspension in methanol/ethanol is not uniform and the catalyst particles settle at the bottom of the reactor vessel.

In certain illustrative embodiments, the presently disclosed transesterification catalysts can be active at significantly less severe conditions than other heterogeneous catalyst systems. For example, other methanolysis transesterification heterogeneous catalysts require temperatures from 150 to 250 degrees C. and pressures of 300to 400 psi. These operating conditions require that other processes using heterogeneous catalysts are carried out in fixed bed reactors.

In contrast, methanolysis transesterification using the presently disclosed transesterification catalysts to manufacture biodiesel requires temperatures in the range from 40 to 70 degrees C. and atmospheric pressure conditions, in certain illustrative embodiments. Similarly, transesterification using the presently disclosed transesterification catalysts to react, for example, dodecanol or other higher alcohols and triglycerides to manufacture biolubricants requires temperatures up to and slightly above 100degrees C. and atmospheric pressure conditions, in certain illustrative embodiments. For these services, the presently disclosed transesterification catalysts can be used in CSTR, fluidized bed and PFR reactor systems.

To ensure complete conversion of triglycerides, alcohol is added in excess of stoichiometric requirements, for instance 2 to 4 times that required to ensure the complete conversion of triglycerides to alkyl ester, in certain illustrative embodiments.

Furthermore, the presently disclosed transesterification catalyst is an efficient catalyst in that it can be reusable. The presently disclosed transesterification catalysts can also be used in existing transesterification process equipment without major revamping.

The presently disclosed transesterification catalysts can be used for manufacturing ASTM D 6751 biodiesel and Technical Grade glycerin as well as biolubricants. Also, the presently disclosed transesterification catalysts do not need water wash for post reaction treatment and does not require steps such as pH neutralization to cleanse products.

In order to facilitate a better understanding of the presently disclosed subject matter, the following examples of certain aspects of certain embodiments are given. In no way should the following examples be read to limit, or define, the scope of the presently disclosed subject matter.

EXAMPLE 1

UMAKAT preparation is illustrated as a double metal salt catalyst with ceramic base support of zirconium oxide. In a typical catalyst preparation, 3 moles of Group 1 metal hydroxide, in this Example potassium hydroxide, is mixed with 1 mole of a Group 2 metal hydroxide, in this Example calcium hydroxide, and dissolved in dilute phosphoric acid. The reaction of the metal hydroxides and the acid produces a double metal salt. This is then heated in a temperature range from 60 to 90 degrees C. As a result, a white precipitate is formed which is then washed with water and mixed with 4 moles of zirconium oxide powder. This material is calcined at 400-500 degrees C. for a minimum of 4 hours. The resulting material is porous, solid and heterogeneous with nanometer-sized pores with a structure that has significant surface area.

EXAMPLE 2

This example describes the preparation of fatty acid methyl esters by transesterification of soybean oil with methanol using the presently disclosed transesterification catalysts. In a typical reaction, commercial soybean oil (100gms) and methanol (oil to methanol molar weight ratio of 1:6) and the presently disclosed transesterification catalysts (2 to 6 wt % of the presently disclosed transesterification catalysts in oil) were charged to a 500 ml glass beaker and stirred at a speed of 300 to 500 rpm at a temperature of 60-80 degrees C. for about 10 to 30 minutes. It was then allowed to cool.

The the presently disclosed transesterification catalyst was separated by filtration from the mixture of reaction products. The product mixture included unreacted methanol plus an upper layer of methyl ester and a lower layer of glycerin. Then, unreacted methanol was separated from each layer by distillation. The methyl ester was tested in a gas chromatograph.

The methyl ester analysis report is summarized in Table 1 below along with the ASTM spec for biodiesel.

TABLE 1

|  | UMAKAT | ASTM SPEC |
| --- | --- | --- |
| Water & Sediment | 0.000 | .05 max |
| Cetane Number | 47.8 | 47 min |
| Cold Soak Filtration | 90 seconds for 300 ml | 300 sec max |
| Free glycerin | 0.005% | .02 max |
| Total glycerin | 0.191% | .24 max |
| Calcium, ppm | <1 | — |
| Magnesium, ppm | <1 | — |
| Sodium, ppm | <1 | — |
| Potassium, ppm | <2 | — |

Table 1 generally shows: no water and sediments are present in the alkyl ester product, only trace amounts of metals solids are present, and, as measured by the amount of glycerin in the product, the reaction is essentially complete conversion to methyl ester. The biodiesel made with the presently disclosed transesterification catalysts was also assessed via the Cold Soak Filtration Test. In this test, a biodiesel liquid sample is chilled to below 32 degrees F. for 16 hours, restored to room temperature and passed thru a 0.5 micron filter. This ASTM test is passed if the filtration is complete within 300 seconds. The biodiesel of the presently disclosed transesterification catalysts passed thru the filter in 90 seconds.

Different oils and fats were tested for oil conversion to methyl ester using UMAKAT and the results are tabulated in the following table:

TABLE 2

| Test No. | Oil/Fat | Alcohol | % Oil conversion | Notes |
| --- | --- | --- | --- | --- |
| 2 | Canola Oil | Methanol | 97.7 | — |
| 3 | Yellow grease | Methanol | 96.8 | — |
| 4 | Coconut Oil | Methanol | 98.2 | — |
| 5 | Cottonseed Oil | Methanol | 97.5 | — |
| 6 | Chicken Fat | Methanol | 97.2 | High Free Fatty Acid ("FFA") Oil first esterified with acid catalyst |

Table 2 shows that the presently disclosed transesterification catalyst is effective for a wide variety of oils and fats.

FIGS. 2 thru 5 are heterogeneous catalytic kinetics graphs showing how the reaction proceeds at different temperatures, methanol ratios, and catalyst weight concentrations.

In certain illustrative embodiments, the presently disclosed transesterification catalysts can be easily separated from reactants and products and reused, no leaching of metal ions into the reactant mixture was observed, and processing temperature and pressure of the presently disclosed transesterification catalysts are at moderate conditions which are significantly less severe than other heterogeneous catalytic transesterification processes.

Additionally, in certain illustrative embodiments the presently disclosed transesterification catalysts can be used to process low cost/unrefined oils and/or fats containing impurities that, for example, cause discoloration of the feedstock. Further, post reaction process waste is reduced as neutralization and water wash of products are not required. Relative to other catalysts and processes, the presently disclosed transesterification catalyst is highly active at comparatively low temperature and pressure. Also, the presently disclosed transesterification catalyst produces much fewer impurities in the alkyl ester and glycerin products and thus the products are much cleaner at the end of the reaction. Further, no pH neutralization water wash is required and salts from glycerin neutralization do not end up in the alcohol distillation column. Finally, transesterification facilities of the presently disclosed transesterification catalysts are comparatively lower in cost to install, maintain and operate.

As used herein, the term "in the range from" and like terms is inclusive of the values at the high and low end of said ranges, as well as reasonable equivalents.

While the disclosed subject matter has been described in detail in connection with a number of embodiments, it is not limited to such disclosed embodiments. Rather, the disclosed subject matter can be modified to incorporate any number of variations, alterations, substitutions or equivalent arrangements not heretofore described, but which are commensurate with the scope of the disclosed subject matter.

Additionally, while various embodiments of the disclosed subject matter have been described, it is to be understood that aspects of the disclosed subject matter may include only some of the described embodiments. Accordingly, the disclosed subject matter is not to be seen as limited by the foregoing description, but is only limited by the scope of the appended claims.

What is claimed is:

1. A method of preparing alkyl ester using a transesterification catalyst, the method comprising:
    providing a transesterification catalyst having the formula $Z_xQ_y(PO_4)_n H_2O$, wherein:
    Z is selected from the group consisting of sodium and lithium,
    Q is selected from the group consisting of calcium and barium,
    x is a rational number in the range from 0.5 to 4,
    y is a rational integer in the range from 2 to 8, and
    n is a rational integer in the range from 4 to 8; and wherein the transesterification catalyst having the formula $Z_xQ_y(PO_4)_n H_2O$ is supported on a ceramic substrate; and
    reacting one or more triglycerides and an alcohol in the presence of the catalyst and converting the triglycerides and alcohol to alkyl ester and glycerin.

2. The method of claim 1, wherein the triglycerides comprise triglyceride-containing fats and/or oils.

3. The method of claim 1, wherein the converting of triglycerides comprises producing essentially complete conversion of the triglycerides to alkyl ester and glycerin.

4. The method of claim 1, further comprising:
    separating the glycerin from the alkyl ester and catalyst;
    filtering the alkyl ester to recover the catalyst; and
    distilling the unreacted alcohol from the alkyl ester and the glycerin.

5. The method of claim 1, wherein the method is at least partially performed in a continuous stirred tank reactor.

6. The method of claim 1, wherein the method is at least partially performed in a fixed bed reactor.

7. The method of claim 1, wherein the method is at least partially performed in a fluidized bed reactor.

8. The method of claim 1, wherein the alkyl ester is capable of being used as biodiesel fuel.

9. The method of claim 1, wherein the alkyl ester is capable of being used as biodiesel additive to conventional diesel fuel.

10. The method of claim 1, wherein the alkyl ester is capable of being used as a biolubricant additive to other lubricants.

11. The method of claim 1, wherein the alkyl ester is capable of being used as a biolubricant.

* * * * *